US010456083B2

(12) United States Patent
Helms-Tillery et al.

(10) Patent No.: US 10,456,083 B2
(45) Date of Patent: Oct. 29, 2019

(54) SYSTEM AND METHOD FOR CORTICAL MAPPING WITHOUTH DIRECT CORTICAL STIMULATION AND WITH LITTLE REQUIRED COMMUNICATION

(71) Applicants: Stephen Helms-Tillery, Phoenix, AZ (US); Remy Wahnoun, Paris (FR)

(72) Inventors: Stephen Helms-Tillery, Phoenix, AZ (US); Remy Wahnoun, Paris (FR)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 612 days.

(21) Appl. No.: 15/147,843

(22) Filed: May 5, 2016

(65) Prior Publication Data

US 2016/0331264 A1    Nov. 17, 2016

Related U.S. Application Data

(60) Provisional application No. 62/162,431, filed on May 15, 2015.

(51) Int. Cl.
  *A61B 5/04* (2006.01)
  *A61B 5/00* (2006.01)
  *A61B 5/0478* (2006.01)
  *A61B 5/0484* (2006.01)

(52) U.S. Cl.
  CPC .......... *A61B 5/6868* (2013.01); *A61B 5/0478* (2013.01); *A61B 5/0484* (2013.01); *A61B 5/4005* (2013.01)

(58) Field of Classification Search
  CPC ........... A61B 5/00; A61B 5/04; A61B 5/0478; A61B 5/6868; A61B 5/0484; A61B 5/4005
  See application file for complete search history.

(56) References Cited

U.S. PATENT DOCUMENTS

| 2005/0182456 | A1  | 8/2005  | Ziobro et al. |              |
|--------------|-----|---------|---------------|--------------|
| 2011/0015469 | A1* | 1/2011  | Walter        | A61M 21/02   |
|              |     |         |               | 600/27       |
| 2012/0022392 | A1* | 1/2012  | Leuthardt     | A61B 5/048   |
|              |     |         |               | 600/544      |
| 2015/0313497 | A1* | 11/2015 | Chang         | A61B 5/048   |
|              |     |         |               | 600/544      |

OTHER PUBLICATIONS

Kim et al., "Distributed functions of detection and discrimination of vibrotactile stimuli in the hierarchical human somatosensory system." Front Hum Neurosci. Jan. 21, 2015;8:1070 (Year: 2015).*

(Continued)

*Primary Examiner* — Eric J Messersmith
(74) *Attorney, Agent, or Firm* — Quarles & Brady LLP (57) ABSTRACT

An apparatus for cortical mapping and method for using same are disclosed. The apparatus comprises a ECoG electrodes array, a stimulation pad, a neural interface processor, and a computing device for mapping eloquent cortical regions of a subject's brain without using exogenous stimulation and with high resolution.

20 Claims, 7 Drawing Sheets

(56) References Cited

OTHER PUBLICATIONS

Nelson, et al. "Activation in SI and SII; the influence of vibrotactile amplitude during passive and task-relevant stimulation" Brain Res Cogn Brain Res. Apr. 2004;19(2):174-84. (Year: 2004).*
Chung et al., "Investigation of cortical activation patterns in response to the inter-digit vibrotactile stimulation," 2012 12th International Conference on Control, Automation and Systems, JeJu Island, 2012, pp. 2038-2041. (Year: 2012).*
Ohara et al., "Movement-related change of electrocorticographic activity in human supplementary motor area proper," Brain. Jun. 2000;123 ( Pt 6):1203-15. (Year: 2000).*
T. Allison, "Localization of Sensorimotor Cortex in Neurosurgery by Recording of Somatosensory Evoked Potentials", Yale J Biol Med, vol. 60, pp. 143-150, 1987.
W.T. Blume et al., "Properties of After-Discharges from Cortical Electrical Stimulation in Focal Epilepsies", Clin Neurophysiol, vol. 115, pp. 982-989, 2004.
G. Cruccu et al, "Recommendations for the Clinical Use of Somatosensory-Evoked Potentials", Clin Neurophysiol vol. 119, No. 8, pp. 1705-1719, 2008.
H.C. Dijkerman et al., "Somatosensory Processes Subserving Perception and Action", Behav Brain Sci, vol. 30, No. 2, pp. 189-239, 2007.
M. Eimer et al., "Modulations of Early Somatosensory ERP Components by Transient and Sustained Spatial Attention", Exp Brain Res, vol. 151, No. 1, pp. 24-31.
A. Fedorov et al, "3D Slicer as an Image Computing Platform for the Quantitative Imaging Network", Magnetic Resonance Imaging, vol. 30, No. 9, pp. 1323-1341, 2012.
M. Fukuda et al, "Somatosensory-Related Gamma-, Beta- and Alpha-Augmentation Precedes Alpha- and Beta-Attenuation in Humans", Clin Neurophysiol, vol. 121, No. 3, pp. 366-375, 2010.
H. Hamalainen et al, "Human Somatosensory Evoked Potentials to Mechanical Pulses and Vibration: Contributions pf SI and SII Somatosensory Cortices to P50 and P100 Components", Electroencephalography and Clin Neurophysiol, vol. 75, pp. 13-21, 1990.
K. Inui et al, "Serial Processing in the Human Somatosensory System", Oxford Journals, Cerebral Cortex, vol. 14, No. 3, pp. 851-857, 2004.
C. Kalberlah et. al., "Dynamic Casual Modeling Suggests Serial Processing of Tactile Vibratory Stimuli in the Human Somatosensory Cortex—An FMRI Study", Neuroimage, vol. 74, pp. 164-171, 2013.
M. Liang et al., "Parallel Processing of Nociceptive and Non-Nociceptive Somatosensory Information in the Human Primary and Secondary Somatosensory Cortices: Evidence from Dynamic Causal Modeling of Functional Magnetic Resonance Imaging Data", J Neurosci, vol. 31, pp. 8976-8985, 2011.
E. Maris et. al., "Nonparametric Statistical Testing of EEG- and MEG-Data", J Neurosci Methods, vol. 164, pp. 177-190, 2007.
C. Neuper et. al., "Event-Related Dynamics of Cortical Rhythms: Frequency-Specific Features and Functional Correlates", Int J Psychophysiol, vol. 43, pp. 41-58, 2001.
S. A. Overduin et al., "Distributed Digit Somatotopy in Primary Somatosensory Cortex", NeuroImage, vol. 23, pp. 462-472, 2004.
G. Pfurtscheller et al., Event-Related EEG/MEG Synchronization and Desynchronization: Basic Principles, Clin Neurophysio, vol. 110, pp. 1842-1857, 1999.
G. Pfurtscheller et al., "Distinction of Different Fingers by the Frequency of Stimulus Induced Beta Oscillations in be Human EEG", Neurosci Lett, vol. 307, pp. 49-52, 2001.
G. Pfurtscheller et al., "Spatiotemporal Patterns of Beta Desynchronization and Gamma Synchronization in aorticographic Data During Self-Paced Movement" Clin Neurophsiol, vol. 114, pp. 1226-1236, 2003.
G. Pollok, et al, Rapid Mapping of Finger Representations in Human Primary Somatosensory Cortex Applying Neuromagnetic Steady-State Responses, NeuroReport, vol. 13, No. 2, pp. 235-238, 2002.

M. Privitera, "Current Challenges in the Management of Epilepsy", Am J Manag Care, vol. 17, Suppl. 7:S, pp. 195-203, 2011.
M. Reuter, et al, "Highly Accurate Inverse Consistent Registration: A Robust Approach", NeuroImage, vol. 53, pp. 1181-1196, 2010.
21. M. Reuter, et al, "Within-Subject Template Estimation for Unbiased Longitudinal Image Analysis", Neurolmage, vol. 61, pp. 1402-1418, 2012.
R. Salmelin et al., "Functional Segregation of Movement-Related Rhythmic Activity in the Human Brain", NeuroImage, vol. 2, No. 4, pp. 237-243, 1995.
G. Schalk et al, "BCI2000: A General-Purpose Brain-Computer Interface (BCI) System", IEEE Trans Biomed Eng, vol. 51, No. 6, pp. 1034-1043, 2004.
R. Schweizer et al., "Finger Representation in Human Primary Somatosensory Cortex as Revealed by High-Resolution Functional MRI of Tactile Stimulation", NeuroImage, vol. 42, pp. 28-35, 2008.
C. Simoes et al, "Functional Overlap of Finger Representations in Human SI and SII Cortices", J Neurophysiol, vol. 86, pp. 1661-1665, 2001.
W. Singer, "Synchronization of Cortical Activity and Its Putative Role in Information Processing and Learning", Annu Rev Physiol, vol. 55, pp. 349-374, 1993.
J.F. Tellez-Zenteno et al., "Long-Term Seizure Outcomes Following Epilepsy Surgery: A Systematic Review and Meta-Analysis", Brain, vol. 128, pp. 1188-1198, 2005.
R. Wahnoun et al, "Delineation of Somatosensory Finger Areas Using Vibrotactile Stimulation, an ECoG Study", Brain and Behavior, vol. 5, No. 10, 2015.
N. Tajbakhsh et al., "Computer-Aided Pulmonary Embolism Detection Using a Novel Vessel-Aligned Multi-Planar Image Representation and Convolutional Neural Networks", MICCAI 2015, vol. 9350, pp. 62-69, 2015.
H. Bouma et al., "Automatic Detection of Pulmonary Embolism in CTA Images", Medical Imaging, IEEE Transactions, vol. 28, No. 8, 1223-1230, 2009.
M. Das et al., "Computer-Aided Detection of Pulmonary Embolism: Influence on Radiologists' Detection Performance With Respect to Vessel Segments", Eur Radio!, vol. 18, 1350-1355, 2008.
A. Krizhevsky et al., "ImageNet Classification With Deep Convolutional Neural Networks", Advances in Neural Information Processing Systems, NIPS, vol. 25, pp. 1097-1105, 2012.
J. Liang et al., "Computer Aided Detection of Pulmonary Embolism with Tobogganing and Multiple Instance Classification in CT Pulmonary Angiography", Information Processing in Medical Imaging, pp. 630-641, Springer 2007.
J. Liang et al., "Local Characteristic Features for Computer Aided Detection of Pulmonary Embolism in CT Angiography", Proceedings of the First MICCAI Workshop on Pulmonary Image Analysis, pp. 263-272, 2008.
H. Ozkan et al., "A Novel Method for Pulmonary Embolism Detection in CTA Images", Computer Methods and Programs in Biomedicine, vol. 113, No. 3, pp. 757-766, 2014.
S.C. Park et al., "A Multistage Approach to Improve Performance of Computer-Aided Detection of Pulmonary Embolisms Depicted on CT Images: Preliminary Investigation", Biomedical Engineering, IEEE Transactions, vol. 58, No. 6, pp. 1519-1527, 2011.
A. Prasoon et al, "Deep Feature Learning for Knee Cartilage Segmentation Using a Triplanar Convolutional Neural Network", 2013, MICCAI 2013, pp. 246-253, Springer, 2013.
H.R. Roth et al, "A New 2.5D Representation for Llymph Node Detection Using Random Sets of Deep Convolutional Neural Network Observations", MICCAI 2014, pp. 520-527, Springer, 2014.
X. Wang et al., "Improving Performance of Computer-Aided Detection of Pulmonary Embolisms by Incorporating a New Pulmonary Vascular-Tree Segmentation Algorithm", SPIE Medical Imaging. pp. 83152U-83152U, International Society for Optics and Photonics, 2012.
E.S. Connolly et al, "Fundamentals of Operative Techniques in Neurosurgery", Thieme, 2nd ed., pp. 283-288, 2010.
W. Penfield et al., "Somatic Motor and Sensory Representation in the Cerebral Cortex of Man as Studied by Electrical Stimulation" Brain, vol. 60, pp. 389-443, 1937.

(56) References Cited

OTHER PUBLICATIONS

J. Ruben et al., "Somatotopic Organization of Human Secondary Somatosensory Cortex", Cerebral Cortex, pp. vol. 11, No. 5, 463-473, 2001.
http://www.cad-pe.org, accessed on Jun. 9, 2016.
R. Oostenveld et al., "FieldTrip: Open Source Software for Advanced Analysis of MEG, EEG, and Invasive Electrophysiological Data", Computational Intelligence and Neuroscience, vol. 2011, No. 3, pp. 1-9, 2011.
Epilepsey Foundation, "Annual Report 2013", pp. 24-52, 2013.

* cited by examiner

SYSTEM AND METHOD FOR CORTICAL MAPPING WITHOUTH DIRECT CORTICAL STIMULATION AND WITH LITTLE REQUIRED COMMUNICATION

CROSS REFERENCE TO RELATED APPLICATIONS

This application claims priority to provisional application Ser. No. 62/162,431 filed on May 15, 2015.

STATEMENT REGARDING FEDERALLY SPONSORED RESEARCH

N/A

BACKGROUND

Approximately 65 million individuals worldwide are living with epilepsy. The first and most common form of relief relies on anti-epileptic drugs. However, one-fourth to one-third of the cases do not become seizure-free from drug therapy alone. In these situations, surgery may be an option if a single, localizable focus can be identified and safely removed.

To obtain a broad sense of the origins and types of seizures, neural activity is first monitored using an electroencephalography (EEG) system through scalp recordings of brain activity (Phase I). If the seizures appear to be potentially focal and unilateral, surgically implanted electrocorticographic (ECoG) electrodes on the cortical surface, or depth electrodes for deep foci, are used to monitor cortical activity during seizures and further define the epileptic foci (Phase II). The decision for surgical resection or intervention depends on the data from this invasive monitoring strategy that delineates the epileptogenic zone to ensure that resection of the seizure foci will not significantly impact neurological functions. During Phase II monitoring, in addition to seizure localization, several procedures are used to define areas of eloquent cortex, which is used to describe areas of cortex that—if removed—will result in loss of sensory processing or linguistic ability, minor paralysis, or paralysis, and attempt to estimate the cognitive functions possibly affected by respective surgery.

Electrical Cortical Stimulation (ECS) is considered the gold standard for sensorimotor functional delineation of eloquent tissue in the brain. In contrast to continuous monitoring where the electrical current from the brain is passively recorded, electrical current is passed between neighboring electrodes to evoke sensory or motor manifestations. Typically during ECS, 50 Hz square pulse trains are applied lasting two to five seconds. The stimulation current is gradually increased up to 10 mA until a sensory, a motor, or an after-discharge response is elicited.

A bottom-up approach can also be used for the mapping where peripheral nerves are electrically stimulated and evoked responses in the cortical signals are visually observed. However those two techniques have limitations. The somatic response is subjective and interpretative based on the subject's response and direct observation by the tester. Cortical stimulation does not always elicit motor responses in children under ten years of age. For sensory areas, it is often difficult to interpret evoked stimuli. In children, particularly those who are too young or non-verbal due to cognitive dysfunction, interpretation of sensation can be very difficult. Additionally, after-discharges, an unwanted consequence of ECS stimulation, are frequent, and can lead to seizures.

Therefore, it would be desirable to have a system and method for cortical mapping that does not use electrical stimulation but produces resolution comparable with that with electrical stimulation, or require detailed or any communication with the patients during the mapping.

SUMMARY

The present disclosure overcomes the aforementioned drawbacks by providing a system and method that delivers vibration to the skin rather than electrical stimulation to the brain. The vibrations serve as stimulation or cues for movement. For somatosensory cortex mapping, little communication with the subject is required. So is motor cortex mapping if the subject receives movement instructions before the mapping procedures start.

The Applicant's disclosure relates generally to an apparatus for mapping somatosensory and motor cortical regions of a brain of a subject who is undergoing electrocorticoencephalographic (ECoG) recording. In certain embodiments, the apparatus comprises a computing device, a stimulation pad interconnected to said computing device, wherein said stimulation pad is configured to be brought into physical contact with a selected region of the subject's skin; a neural interface processor interconnected to said computing device; and an ECoG electrodes array to be implanted on a surface of the subject's brain, wherein said ECog electrode array is in communication with the neural interface processor.

Additionally, the Applicant's disclosure relates generally to a method for mapping somatosensory and motor cortical regions of a brain of a subject who is undergoing electrocorticoencephalographic (ECoG) recording. In certain embodiments, the method comprises the steps of providing an apparatus comprising a computing device, a stimulation pad interconnected to said computing device, a neural interface processor interconnected to said computing device; implanting a ECoG electrodes array on a surface of the subject's brain; contacting said stimulation pad with a selected region of the patient's skin; producing during a first period of time stimulation of said selected region; recording by said neural interface processor a plurality of cortical signals originating in said subject's brain; based upon said plurality of cortical signals, mapping eloquent cortical regions of the subject's brain; generating a 3-D mapping in combination with a plurality of landmark locations of said subject's brain using one or more medical imaging techniques; forming a composite image by overlaying an image of said ECoG electrode array onto said 3-D mapping with said landmark locations; and comparing the mapped eloquent cortical regions to said composite image to reduce a risk of causing brain injury during a surgical remediation of epileptic seizures.

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The system and method disclosed herein can map somatosensory and motor cortexes without direct cortical stimulation or depending on biased interpretation by the subject. Little communication with the subject is required, so the system and method can produce maps even of unresponsive subjects.

Vibratory stimuli are relayed by the lemniscal pathway from the cutaneous mechanoreceptors to the somatosensory cortical areas. Epicritic inputs from the lemniscal system are transmitted from the ventroposteriolateral nucleus of the thalamus to several cortical areas. By mapping the cortical areas in response to the vibratory stimuli, physicians intend to avoid those cortical areas and preserve the functions of those areas when resecting cortical areas responsible for epileptic seizures.

Finger representation in the contralateral primary sensory cortex (SI) covers about a 10-20 mm long cortical strip, following a latero-medial distribution, from the thumb to the small finger with a limited amount of overlap and notable inter-individual variability. As described herein, "about" means a 10% difference in measurement. The secondary sensory cortex (SII) does not seem to follow a topological organization of the fingers or show a strong spatial overlap, and may be involved in bimanual tasks.

Figure 1:
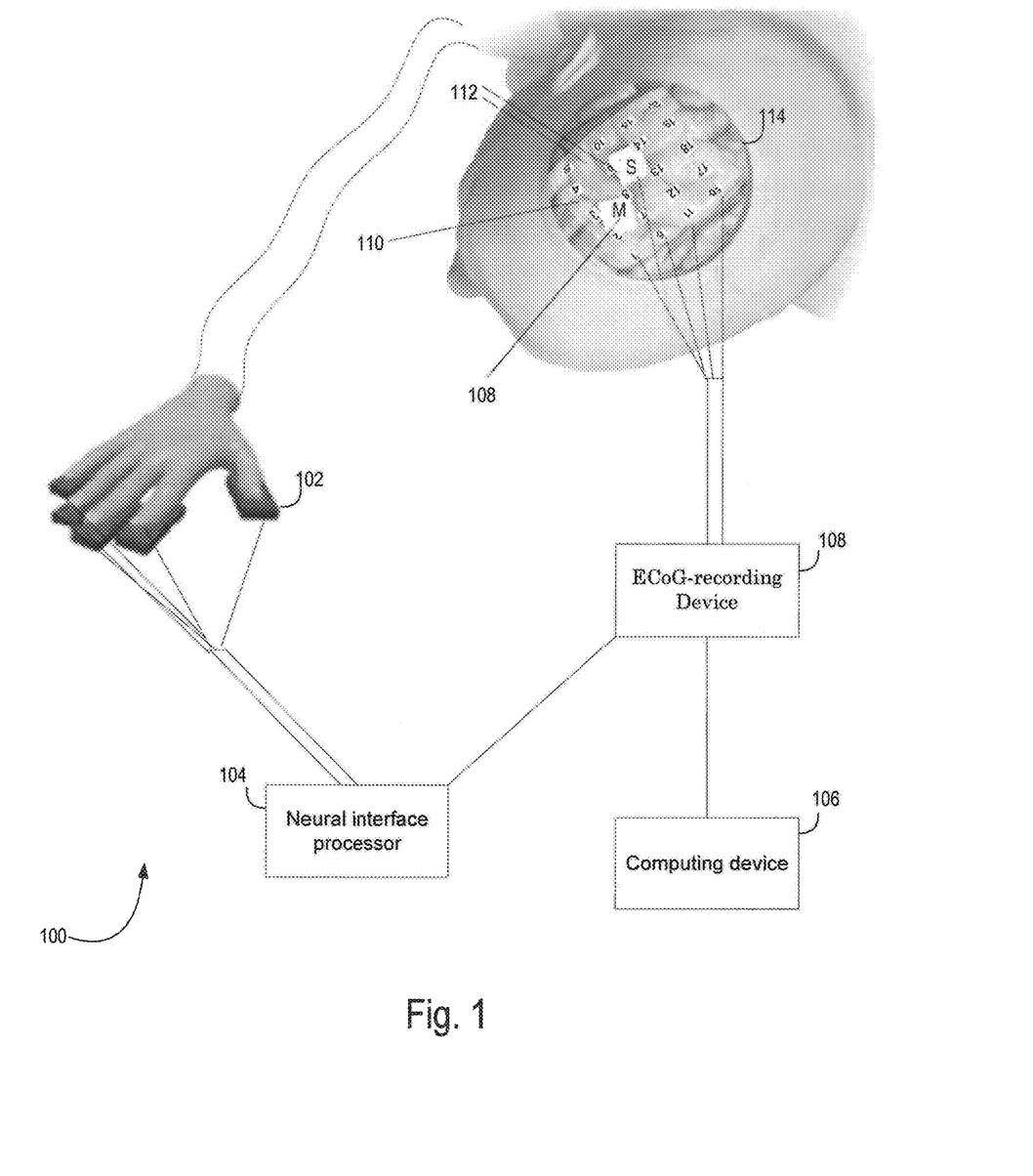
FIG. 1 is a diagram of an example system implemented for somatosensory cortex mapping according to the present application.

Referring now to FIG. 1, an embodiment of an apparatus 100 for mapping somatosensory and motor cortical regions of a brain of a patient who is undergoing electrocorticoencephalographic (ECoG) recording to locate areas of eloquent cortex and reduce a risk of causing permanent brain injury during surgical remediation of seizures is shown here. This embodiment should not be construed as limiting on the invention. A subject's fingers can be placed in a stimulation pad 102. In certain embodiments, the stimulation pad 102 further comprises a plurality of vibration motors 102a and a plurality of force sensitive resistors 102b. In one embodiment, the plurality of vibration motors comprises 5 about 10 millimeter (mm) shaftless vibration motors. In another embodiment, the plurality of force sensitive resistors 102b comprises 5 0.5 inch long force sensitive resistors. The vibration motor produces a small buzzing sensation when pressed to the skin and activated. Vibratory stimulation at ~60 Hz is known to activate a variety of peripheral receptors and thus produce a robust neural response that can be measured as changes in the ECoG signals. Vibrations delivered by the stimulation pad 102 can also serve as cues for movement. For this purpose, the vibrator may comprise a thin-film pressure transducer mounted in container that can be manufactured by rapid prototyping. So when a subject's finger is placed in the device, it can be vibrated for mapping the hand area of somatosensory cortex and monitored for pressure applied by the subject's finger to map the hand area of motor cortex.

Each of the 5 shaftless vibration motors and each of the 5 force sensitive resistors are encased in a customized finger placeholder that can be manufactured using rapid prototyping. Further, each of these 5 finger placeholders is placed on a slotted foam stimulation pad 102. In certain embodiments, the stimulation pad 102 is able to be adjusted in size to accommodate smaller hands for younger patients. Moreover, vibration interference between fingers is able to be reduced in the stimulation pad 102.

A neural interface processor 104 conducts signals to the stimulation pad 102 with respect to the stimulation of vibration, the frequency of vibration, the time period of the vibration, the time period of the vibration interference, and the synchronizing pressure values from the fingers to the cortical signals. Furthermore, the neural interface processor 104 measures delays and rising time of the motors for correction during data analysis. In some embodiments, the neural interface processor comprises a microcontroller, which is able to be programmed and can communicate with a computing device 106. In some embodiments, the computing device 106 is a computer with a customized program encoded. In addition, the neural interface processor 104 comprises an ECoG-recording device 108, which is able to collect digital and analog signals indicating the beginning of a vibratory stimulus or detection of a change in the pressure on the pressure sensor. This enables a quick alignment of the ECoG data with behavioral and stimulus events at the periphery.

In certain embodiments, the vibrations stimulate the fingers and may also serve as cues for the subject to move the fingers. Neural activities in response to the stimulation or the cues are recorded with an ECoG electrodes array 110. The ECoG electrodes array 110 is implanted directly on the brain that is exposed by a surgical opening 114. Compared with EEG recordings, ECoG electrodes lie on the surface of the brain, providing increased spatial resolution and higher signal to noise ratio. Array locations can be selected from the observations during Phase I monitoring and no additional implants are required. To map the somatosensory and the motor cortexes, the array covers the region of primary motor cortex 108 and primary sensory cortex 112. The ECoG signals are detected and recorded with a ECoG-recording device 108 and then sent to computing device 106. The computing device 106 processes the signals to determine neural activities in response to the stimulation or cues, determine specific electrodes in the ECoG electrodes array 110 that have detected the neural activities, and displays the locations of the specific electrodes overlaid on brain images acquired with a medical imaging modality. Such a modality can be computed tomography (CT) or magnetic resonance imaging (MRI).

Figure 2:
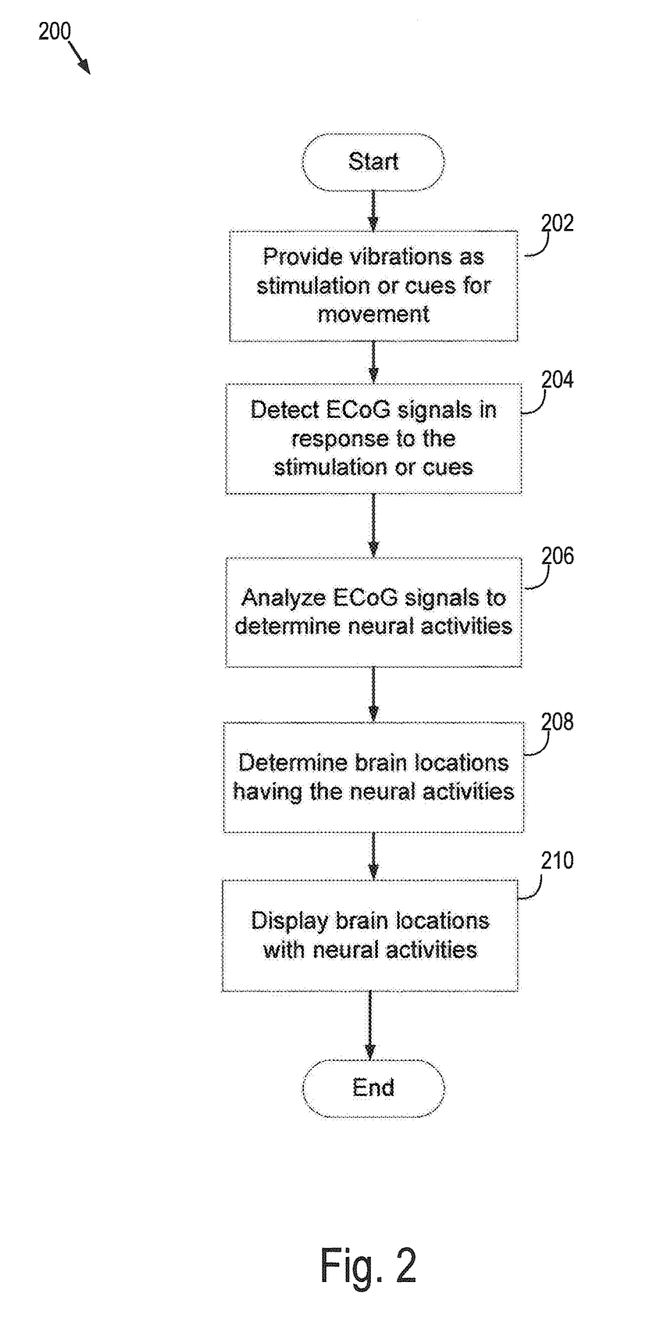
FIG. 2 is a flowchart of an example method of somatosensory cortex mapping implemented according to the present application.

Referring to FIG. 2, a flowchart 200 of an example method implemented according to the present application is provided. In step 202, vibrations are provided to stimulate digits of a subject or as cues for movement of the digits. In step 204, ECoG signals of the brain in response to the stimulation or the cues are detected and recorded by the neural interface processor 104. The recorded ECoG signals are transferred to the computing device 106 for further calculation and statistical analysis. In step 206, the ECoG signals are analyzed to determine neural activities evoked by the stimulation or the cues. In step 208, brain locations having those evoked neural activities are determined and mapped. In step 210, for better visualization, the locations having the neural activities are overlaid on images acquired with a medical imaging modality, such as CT or MRI. These applications often include landmark-based image registration, segmentation of brain structures, prospective subject positioning in longitudinal imaging. Landmarks are specific structures with distinguishable morphological characteristics. The most basic method for locating anatomical landmarks on MM is manual placement by a trained operator.

The ECoG signals are processed to reduce noise and prepare for analysis. One source of noise is the fluctuation in the background cortical recordings. Background cortical recordings show a significant amount of natural fluctuations due to variations in arousal, focus, or uncontrolled external stimuli during the course of the mapping, all of which can affect the mapping outcome. To minimize this effect, as many trials as possible can be recorded for each condition and for all statistical tests; baseline correction is performed from 150 ms to 10 ms before stimulation. The computing device can also determine which electrodes have responses associated with the tactile stimulation or the movement by rapidly scanning activities across the entire set of electrodes. It can also register the physiological results from the ECoG signals with anatomical images obtained by MRI and CT.

Figure 3:
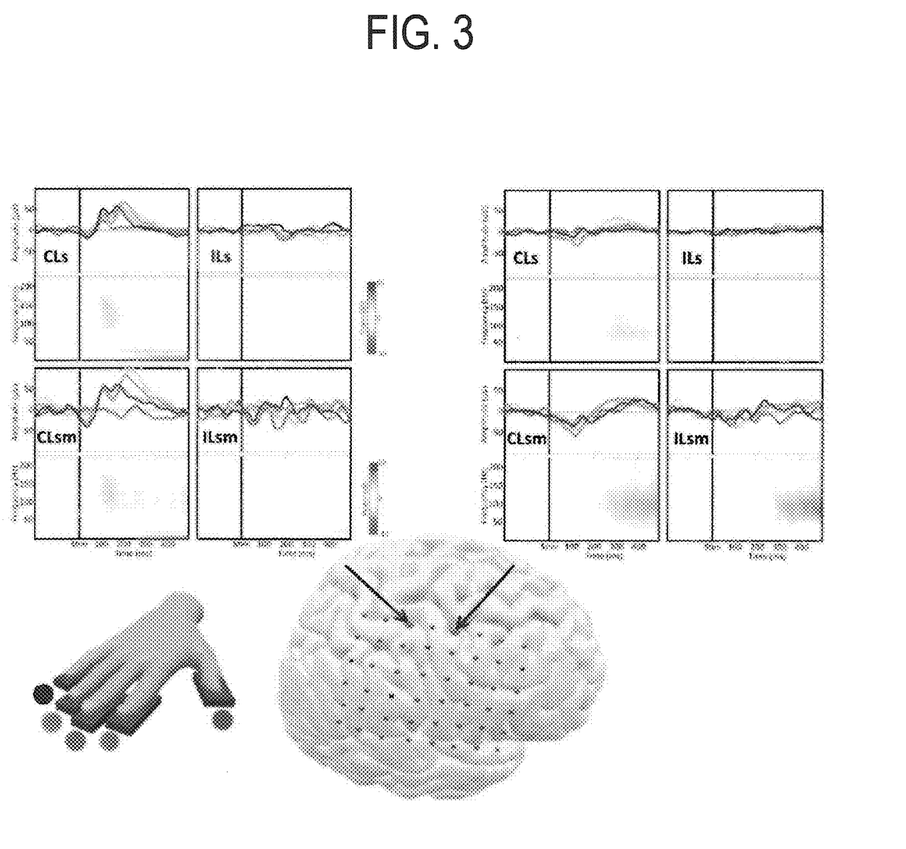
FIG. 3 is a diagrammatic plot illustrating Temporal and Spectrotemporal response to vibrotactile stimuli on Sub1. The two panels represent the average response to vibrotactile stimulation under four experimental conditions (CLs: Contralateral sensory, CLsm: Contralateral sensorimotor, ILs: Ipsilateral Sensory, and ILsm: Ipsilateral Sensorimotor). The top of each subpanel represents the average evoked response; the bottom part shows its average time-frequency representation over the five fingers (ERS in red, ERD in blue). Traces are color coded per stimulated finger as shown in the bottom-left sketch.

Referring to FIG. 3, in certain embodiments, a subject performs two tasks: a sensory only (s) and a sensorimotor (sm) task performed contralaterally (CL) or ipsilaterally (IL) to the recording grids of interest, leading to four experimental conditions: CLs, CLsm, ILs, and ILsm. In the sensory only task, while patients sat comfortably in their hospital bed, their fingers were placed on the stimulation pad 102 designed to individually stimulate the fingers. One hand at a time, the patients' fingers were randomly vibrated for a period ranging from 100 ms to 500 ms, with an inter-stimulation interval ranging from is to 1.4 s. In the sensorimotor task, the stimulation remained the same, but the patients were instructed to attend to the stimulus by pressing the corresponding finger on the stimulation pad 102. The time allowed for motor response was set to 4 s, with an inter-trial interval of 1.5 s. Each set consisted of 50 trials (ten per finger), after which hands were switched. Up to 30 sets over a period of several days according to the patients' physical and mental status are recorded.

In certain embodiments, the signals are analyzed in the time domain. Time domain analysis typically focuses on evoked potentials, averaging cortical responses over large numbers of trials. This procedure enhances time locked components and reduces the impact of non-related activity. Somatosensory Evoked Potentials (SEPs) can be elicited by stimulating peripheral nerve fibers.

In other embodiments, the ECoG signals can also be analyzed in the time-frequency domain. Time-frequency domain analysis expands the analysis of evoked responses to changes in oscillatory activity induced by stimulation. Evoked Response Synchronization (ERS) and Evoked Response Desynchronization (ERD) correspond respectively to an increase or decrease of the power of oscillations in a given band. ERS may emerge as the result of a surge of concurrent activity in a network while ERD may arise as the result of a decreased correlation. Smaller functional networks may exhibit higher ERS frequencies than larger areas.

Referring again to FIG. 3, the postcentral-medial (left panel) electrode's response to contralateral sensory stimulation begins with a N40 peaking across fingers at an average at 38 ms, followed by P100 (108 ms), N140 (138 ms), and P200 (186 ms), before returning to baseline levels. The frequency domain response shows a wide broadband increase in the high frequency range coinciding with the first peak, followed by a low frequency rebound. Similar responses for this electrode can be seen in the contralateral sensorimotor task, with larger amplitudes. The precentral-medial electrode (right panel) presents a N100 followed by a high frequency increase in both contralateral tasks, as well as a delayed high frequency increase in the ILsm task.

Figure 4:
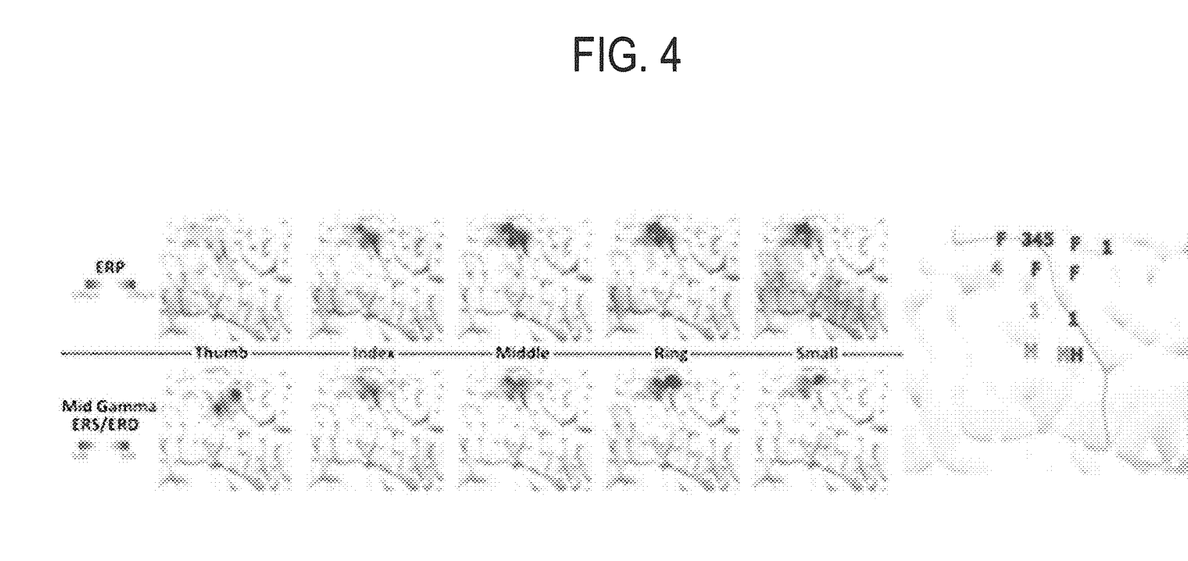
FIG. 4 is a diagrammatic plot illustrating elicited response (80-120 ms) in the temporal (Left-top), and spectrotemporal (Left-bottom) domains to vibratory contralateral stimulation of the five fingers, and clinical electrical mapping (Right), in which labels represent clinical mapping results (H: Hand, F: Fingers, numbers represent individual digits, s/m respectively sensory and motor).

Referring to FIG. 4, across subjects, the time-frequency domain showed more spatially localized responses, as shown for Sub1 in the left panel. For this subject, both domains presented the accepted precentral latero-medial somatotopic distribution. However, in the frequency domain, the elicited response is more demarcated from the background and more spatially focused. For this subject, clinical mapping (right panel) located broad fingers/hand regions, but in some cases, postcentral stimulation lead to motor responses.

A cluster-based nonparametric permutation test can be used to address non-Gaussian distributions of the ECoG signals and multiple comparisons issues. A multiple comparison problem arises when a large number of statistical tests are simultaneously performed. It can be minimized with the Bonferonni correction. The nonparametric permutation test takes advantage of the significant correlation between adjacent electrodes to lower the family-wise error rate in the Bonferonni correction and at the same time increase sensitivity of the test. This method results in clusters of adjacent time-domain or time-frequency-domain samples, depicting significant activation originating from the precentral cortex or above the central sulcus. Cluster detection can be applied on the full band spectrum, in addition to a per-band basis. This can lead to cluster localization in the time-frequency-space domain instead of time-band-space domain and may provide information on the spectral evolution of elicited activity.

Across all subjects, conditions and stimulated fingers, clustering in the spectrotemporal domain led to 151 significant ($p \leq 0.05$) clusters appearing within 240 milliseconds after stimulation (Table 2); 40.4% of which started as contralateral ERS above 65 Hz, while 17.9% corresponded to a contralateral ERD below 30 Hz. The smaller number seen in CLsm as compared to CLs seems to originate from a higher residual pre-stimulus activity, preventing some clusters from exhibiting significance at this level. Significant clusters emerged earlier in the most active ERD band (MidG: 118.1 ms) than in the most active ERD band (Beta: 143.4 ms).

TABLE 2

Number of significant ERS/ERD clusters across conditions and subjects ($p \leq 0.05$)

|      | Alpha | Beta | LowG | MidG | HigG |
|------|-------|------|------|------|------|
| CLs  | 2/8   | 0/13 | 0/2  | 29/1 | 11/1 |
| CLsm | 3/1   | 1/5  | 1/1  | 14/1 | 7/0  |
| ILs  | 4/2   | 3/2  | 3/1  | 4/3  | 10/2 |
| ILsm | 4/1   | 1/1  | 1/2  | 2/2  | 1/1  |

Figure 5:
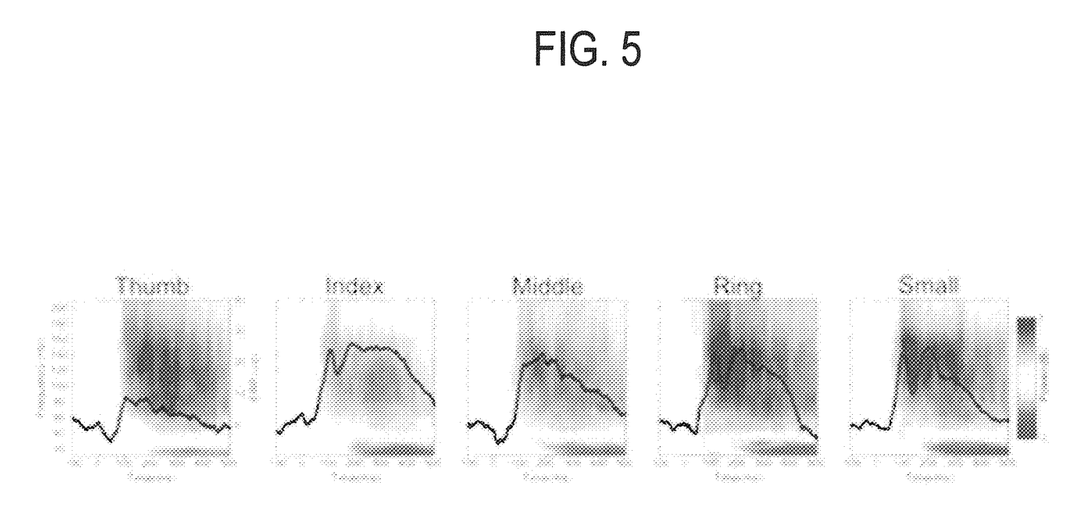
FIG. 5 is a diagrammatic plot illustrating time-frequency evolution of electrodes with significant Mid Gamma clusters, and associated Event Related Potentials (black traces), averaged across subjects.

Referring to FIG. 5, in certain embodiments, due to the latency jitter often observed in the time domain and the inherent high background noise in our patient population, the study is focused on in the time-frequency domain, and specifically the Mid-Gamma event related synchronization. Across subjects, the electrodes presenting significant clusters in the MidG band presented an early ERS (red) followed by a late ERD (blue).

Figure 6:
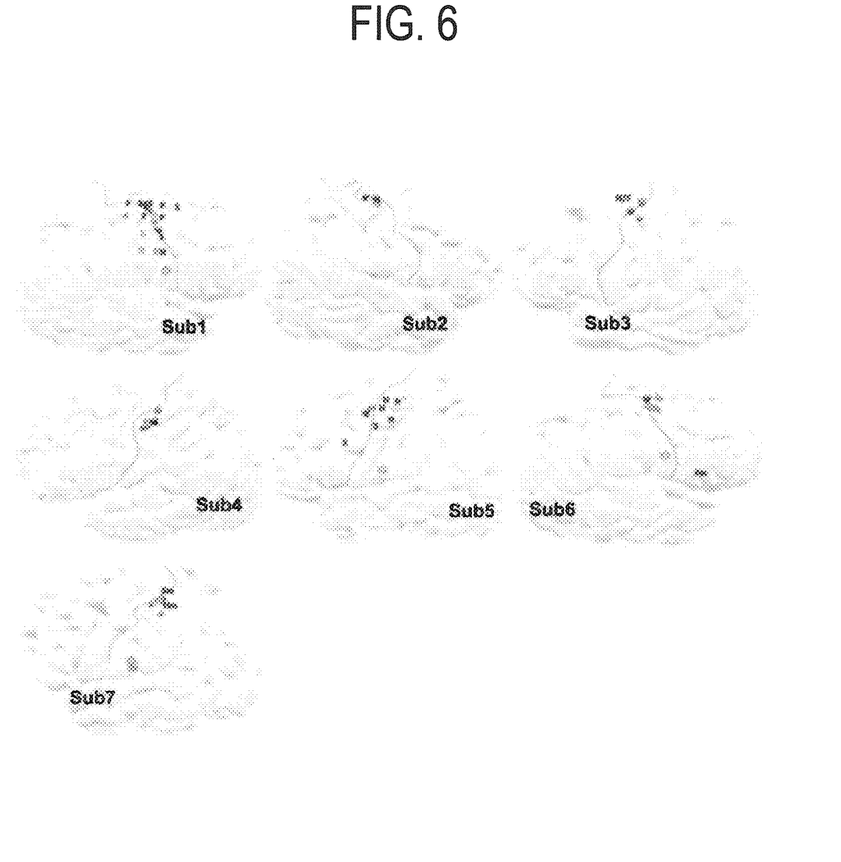
FIG. 6 is a diagrammatic plot illustrating clinical electrical mapping vs. vibrotactile sensory mapping of the contralateral fingers. Clinical mapping results are indicated with numbers and letters on the cortical surface (H: Hand, F: Fingers, 1-2-3-4-5 individual digits, s/m sensory/motor). Superimposed on those cortical maps, the colored spheres (as in FIG. 3) represent one result from the vibrotactile mapping. Stars indicate electrodes with a late lateral response described below.

Referring to FIG. 6, in order to evaluate Mid-Gamma activations for each digit, the tridimensional location of electrodes belonging to the most significant cluster are weighted by their absolute power and represented by the colored spheres on the cortical models. Across subjects, the vibrotactile task led to clustered localizations of the contralateral fingers, spanning less than 20 mm. In certain embodiments, the estimated digital areas were located posteriorly or above the central sulcus, in agreement with anatomical expectations. In comparison, electrical stimulation leads to broad representations of the hand/digits and seldom located sensory areas.

Figure 7:
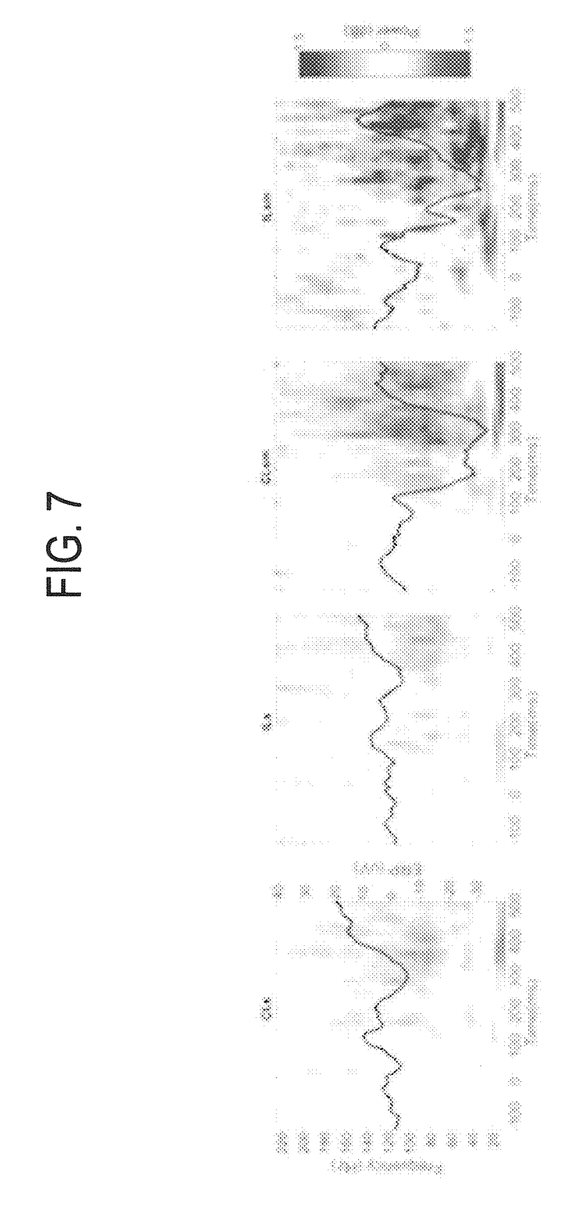
FIG. 7 is a diagrammatic plot illustrating late lateral response averaged over four subjects.

Referring to FIG. 7, in certain embodiments, some subjects underwent a sensorimotor task requiring a finger press in response to the vibrotactile stimuli. For those subjects, an additional broadband response was detected. These late responses, localized in the electrodes marked in FIG. 6 with a yellow star, were stronger under the sensorimotor task than in the sensory only task. Their near-Sylvian location and the delay to the initial response are relatively consistent with the secondary somatosensory areas and their delayed activation seems to imply a secondary processing or motor planning. The relation of the frequency response with respect to two late negative ERP peaks is also observed.

The vibrators allow single digit stimulation and can elicit reliable event-related potential (ERP), ERD and ERS responses, independently of subject wakefulness and mental capacity. Evoked response potentials in the time domain are often degraded by interictal background noise and jitter, while the frequency representations show more consistency. The clustering-based statistical approach—taking into account adjacency relationships in time, frequency, and space—can reliably detect significant ERS/ERD clusters in relevant cortical areas within the Mid-Gamma range.

The system and method can also be used to map secondary somatosensory cortex (SII) by focusing on late lateral responses presented in the ECoG signals. Coherence analysis on the single trial level between the medial and the Sylvian activated locations may provide insight on the temporal relationship between the two regions and whether the Sylvian represents a secondary processing or motor planning stage.

Little or no communication is required during the mapping. The subject can even be asleep during the entire mapping procedures.

The system and method disclosed herein can be implemented in real time. The cortical maps can be displayed instantaneously as vibration is delivered to the vibrators. Physicians can evaluate the mapping and determine whether the mapping provides desired results so to avoid repetition of the mapping procedures.

The system and method disclosed herein provides high-resolution cortical mapping. The resolution can be at the single-electrode level. ECoG typically uses electrodes that are 4 mm in diameter spaced by about a centimeter. Micro-ECoG can use sites as small as 100 microns, spaced as closely as 200 microns. So with the system and method disclosed herein, resolution to the level of 200 microns can be achieved. Such a resolution provides much desirable precision required by the resection surgery or post-surgery assessment, unlike functional magnetic resonance imaging.

The vibrators can be placed at any location on the body. So the entire somatosensory homunculus can be mapped with the system and method as disclosed herein.

EXAMPLES

Material and Methods

Twelve patients undergoing Phase II monitoring for epileptic focus resection at Barrow Neurological Institute at Phoenix Children's Hospital participated in this study. The scope of this paper was restricted to subjects (three males, four females, mean age: 11.6 years, range: 5-20 years) for whom either the clinical or the vibrotactile mapping identified finger or hand responses (see Table 1). The remaining subjects were excluded because their ECoG grids were outside the area of interest (two subjects), because clinicians were unable to obtain clinical sensorimotor maps results (two subjects), or because of incomplete recordings (1 subject).

TABLE 1

| | | Age | Tasks | | | | | | Surgical |
| | Gender | (Years) | CLs | ILs | CLsm | ILsm | Wakefulness | Etiology | Alleviation |
|---|---|---|---|---|---|---|---|---|---|
| Sub1 | M | 11.8 | yes | yes | yes | yes | Awake | Tuberous Sclerosis | Multiple resection |
| Sub2 | F | 5.5 | yes | yes | no | no | Awake | Developmental impairment | Local Resection |
| Sub3 | F | 8.3 | yes | yes | no | no | Sleeping | Cortical Dysplasia | Local Resection |
| Sub4 | F | 8.7 | yes | yes | no | no | Awake | Encephalopathy | None |
| Sub5 | M | 10.9 | yes | yes | yes | yes | Awake | Lennox Gastaut syndrome | VNS placement |
| Sub6 | F | 20.1 | yes | yes | yes | yes | Awake | Cortical Dysplasia | Temporal Lobectomy |
| Sub7 | M | 15.8 | yes | yes | yes | yes | Awake | Perinatal depression with Intracranial hemorrhage | Occipital parietal Lobectomy |

All described procedures were approved by Phoenix Children's Hospital Institutional Review Board and written informed consent was obtained by the parents or legal guardians and/or the subjects prior to any procedure.

Grid locations were selected from the observations from Phase I monitoring and no additional implants were placed for this study. Sub3 was asleep during all the experimental recordings.

Patients were implanted with titanium ECoG electrode grids (10 mm inter-contact distance, 4 mm diameter) and/or strips manufactured by Ad-Tech Medical Instruments Corporation (Hartland, Wis.) or Integra LifeSciences (Plainsboro, N.J.) according to clinical needs. In contrast to EEG recordings, ECoG electrodes lie on the surface of the brain, offering increased spatial resolution and higher signal to noise ratio. A Ripple Grapevine amplifier (Salt Lake City, Utah) was used to record the cortical signals at 500 Hz concurrently with the standard clinical setup (XI-Tek EMU 128). The software Bci2000 [Schalk et al., 2004] orchestrated stimulation and data acquisition. An Integra OCS2 Ojemann Cortical Stimulator Integra LifeSciences (Plainsboro, N.J.) was used for the clinical mapping. Three-dimensional models of the patients' brains, grids and landmark locations were obtained using CT and MR scans. The Freesurfer image analysis suite was used for volumetric segmentation and cortical reconstruction [Reuter et al., 2010; Rueter et al., 2012] from MRI images. Grid extraction from CT scans and co-registration with MR scans were achieved with 3D Slicer 4.3 [Fedorov et al., 2012]. Tridimensional models and analysis results were rendered using Blender 2.73 (Blender Foundation). Due to postoperative swelling and the integration of preoperative MM with postoperative CT, the recording grids were realigned radially to match the pial surface. Due to an inferior MRI quality on one subject, the tridimensional model with the closest structural match was used for this subject.

Vibrotactile Stimulator

We designed a finger stimulator (FIG. 3), consisting of five 10 mm shaftless vibration motors (Precision Microdrives) and five 0.5" force sensitive resistors (interlink Electronics), each encased in custom 3D-printed finger placeholders. The individual units were placed on a slotted foam pad, allowing for adjustment to the size variations in our young population, and reducing vibration interference between the fingers. The system was controlled by an Arduino Pro Micro and connected to a computer via USB, allowing bidirectional communication with the recording computer.

A custom made shield was designed to provide sufficient current to the motors and optically isolate the patients from the computer. Bci2000's source code was then modified to interact with the stimulator, triggering vibrations and synchronizing pressure values from the five fingers to the cortical signals. We measured the delay as well as rising time of the motors for correction in the data analysis.

Tasks

Subjects performed two tasks: a sensory only (s) and a sensorimotor (sm) task performed contralaterally (CL) or ipsilaterally (IL) to the recording grids of interest, leading to four experimental conditions: CLs, CLsm, ILs, and ILsm.

In the sensory only task, while patients sat comfortably in their hospital bed, we placed their fingers on a stimulation pad designed to individually stimulate the fingers. One hand at a time, the patients' fingers were randomly vibrated for a period ranging from 100 ms to 500 ms, with an inter-stimulation interval ranging from is to 1.4 s.

In the sensorimotor task, the stimulation remained the same, but the patients were instructed to attend to the stimulus by pressing the corresponding finger on the recording pad. The time allowed for motor response was set to 54 s, with an inter-trial interval of 1.5 s. Each set consisted of 50 trials (ten per finger), after which we switched hands. We recorded up to 30 sets over a period of several days according to the patients' physical and mental status.

Data Analysis

Preprocessing

Data processing and analysis were performed under Matlab 2014b (the MathWorks Inc, Natick Mass.), using the FieldTrip [Oostenveld et al., 2011] toolbox. The Bci2000 sets were imported into Matlab, baseline corrected, and segmented into 2 seconds trial centered on stimulation onset. For sets showing significant common noise, individual channels were re-referenced on a per-grid basis. The resulting trials were then band-pass filtered (two-pass windowed linear-phase FIR) prior to time-only (BP: 1-30 Hz) and time-frequency analysis (BP: 1-230 Hz). A shorter trial interval (−150 ms to 500 ms) was then used for data analysis to reduce boundary effects after filtering and frequency analysis. Time-frequency representation were calculated using a Morlet wavelet transformation with multiplication in the frequency domain (20 ms windows, 1 Hz precision, 7 cycles).

Background cortical recordings show a significant amount of natural fluctuations due to variations in arousal, focus, or uncontrolled external stimuli during the course of the experiment, all of which could affect the experimental outcome. To minimize this effect, we recorded as many trials as possible for each condition and for all statistical tests; baseline correction was performed from 150 ms to 10 ms before stimulation. For time series, the average value over the baseline period was removed from each trial. For time-frequency series, the trial power of each frequency was divided by its baseline value, then subject to a natural logarithmic transformation, resulting in values in decibels.

Statistical Analysis

In this study, we aimed to test for a potential effect of vibrotactile stimulation and locate this effect in the time-frequency domain. A standard way to minimize the multiple comparison problem (arising when performing simultaneously a large amount of statistical tests) involves the Bonferonni correction. This is a very conservative simultaneously test, and little or no sample pairs would show significant effects.

To address non-Gaussian distributions and multiple comparison issues, we used a cluster-based nonparametric permutation test described in [Maris and Oostenveld, 2007]. This test takes advantage of the fact that there is a significant correlation between adjacent time/frequencies/electrodes to lower the FWER, while reaching sensitivity above the Bonferonni correction.

This method results in clusters of adjacent time-space or time-frequency-space samples with significant p-values. We used the maximum p-value of each cluster and ran 1000 Monte Carlo random partitions to calculate significance probability. We analyzed the responses separately, on a per-band basis, defined as Alpha (8-13 Hz), Beta (13-30 Hz), LowG 930-55 Hz), MidG (65-115 Hz) and HigG (125-230 Hz).

The present invention has been described in terms of one or more preferred embodiments, and it should be appreciated that many equivalents, alternatives, variations, and modifications, aside from those expressly stated, are possible and within the scope of the invention. The manuscript enclosed with this disclosure describes additional background, examples, experimental data, and other information, and is incorporated fully herein by reference.

The invention claimed is:

1. A method for mapping somatosensory and motor cortical regions of a brain of a subject who is undergoing electrocorticoencephalographic (ECoG) recording, the method comprising:
   providing an apparatus comprising a computing device, a plurality of stimulation pads interconnected to said computing device, and a neural interface processor interconnected to said computing device;
   implanting an ECoG electrodes array on a surface of the subject's brain;
   contacting a first selected finger of the patient with a first stimulation pad of the plurality of stimulation pads;
   contacting a second selected finger of the patient with a second stimulation pad of the plurality of stimulation pads;
   producing, with the first stimulation pad during a first period of time, stimulation of the first selected finger;
   producing, with the second stimulation pad during a second period of time, stimulation of the second selected finger;
   recording with said neural interface processor, during the first and second periods of time, a plurality of cortical signals originating in said subject's brain;
   based upon said plurality of cortical signals, mapping eloquent cortical regions of the subject's brain; and
   overlaying an image of said ECoG electrode array onto a 3-D mapping of the subject's brain to produce a composite image, said the 3-D mapping including a plurality of landmark locations; and
   correlating the mapped eloquent cortical regions with said composite image to reduce a risk of causing injury to the mapped eloquent cortical regions during a surgical remediation of epileptic seizures.

2. The method of claim 1, wherein producing the stimulation comprises:
   applying an effective amount of vibration to the first and second selected fingers to activate a plurality of peripheral receptors, thereby generating the plurality of cortical signals contralaterally (CL) or ipsilaterally (IL); and
   causing said subject to press downwardly on a force sensitive resistor such that the pressing generates an endogenous controlateral or ipsilateral sensorimotor signal.

3. The method of claim 2, wherein the mapping step comprises scanning a plurality of peripheral neural responses across said ECoG electrodes array to determine which ECoG electrodes have responses associated with either the stimulation or the pressing movement.

4. The method of claim 1, wherein producing the stimulation comprises applying a vibrotactile stimulation.

5. The method of claim 4, wherein the vibrotactile stimulation is at about 60 Hz.

6. The method of claim 1, wherein producing the stimulation comprises producing an interleaved stimulation, such that over a third period of time each stimulation pad of the plurality of stimulation pads is activated for two or more non-consecutive periods of time.

7. The method of claim 1, wherein producing the stimulation comprises activating each of the plurality of stimulation pads about 100 milliseconds (ms) to about 500 ms.

8. The method of claim 1, wherein producing the stimulation comprises activating each of the plurality of stimulation pads for an inter-stimulation interval, wherein said interval lasts about 1 second to about 1.4 seconds.

9. The method of claim 1, wherein implanting the ECoG electrode array comprises implanting an ECoG electrode that is about 4 millimeter (mm) in diameter.

10. The method of claim 1, wherein implanting the ECoG electrode array comprises implanting an ECoG electrode that is about 100 micron in diameter.

11. The method of claim 1, wherein the recording step comprises analyzing, within a mid-gamma frequency range of about 65 Hz to about 115 Hz, the plurality of cortical signals over a third period of time.

12. The method of claim 11, wherein the plurality of cortical signals comprises somatosensory evoked potentials (SEPs).

13. The method of claim 11, wherein the recording step further comprises analyzing the plurality of cortical signals over the third period of time and in connection with changes in a plurality of oscillatory activities, wherein evoked response synchronization (ERS) corresponds to an increase of the plurality of oscillatory activities and evoked response desynchronization (ERD) corresponds to a decrease of the plurality of oscillatory activities.

14. The method of claim 1, wherein the recording step comprises analyzing, within a beta frequency range of about 13 Hz to about 30 Hz, the plurality of cortical signals over a fifth period of time.

15. The method of claim 14, wherein the plurality of cortical signals comprises somatosensory evoked potentials (SEPs).

16. The method of claim 14, wherein the recording step further comprises analyzing the plurality of cortical signals over the fifth period of time and in connection with changes in a plurality of oscillatory activities, wherein evoked response synchronization (ERS) corresponds to an increase of the plurality of oscillatory activities and evoked response desynchronization (ERDS) corresponds to a decrease of the plurality of oscillatory activities.

17. The method of claim 6, wherein the interleaved stimulation comprises at least two rounds of stimulation, wherein each round of stimulation comprises at least one stimulation of the first selected finger and at least one stimulation of the second selected finger.

18. The method of claim 1, wherein the recording step comprises analyzing the plurality of cortical signals according to a clustering-based statistical approach accounting for correlations across at least time and space dimensions.

19. The method of claim 18, wherein the clustering-based statistical approach further accounts for correlations across at least time, space, and frequency dimensions.

20. The method of claim 18, wherein analyzing the plurality of cortical signals comprises performing the clustering-based statistical approach within a mid-gamma frequency range of about 65 Hz to about 115 Hz.

\* \* \* \* \*

UNITED STATES PATENT AND TRADEMARK OFFICE
CERTIFICATE OF CORRECTION

PATENT NO. : 10,456,083 B2  
APPLICATION NO. : 15/147843  
DATED : October 29, 2019  
INVENTOR(S) : Stephen Helms-Tillery and Remy Wahnoun Page 1 of 1

It is certified that error appears in the above-identified patent and that said Letters Patent is hereby corrected as shown below:

On the Title Page

Title, item (54):
SYSTEM AND METHOD FOR CORTICAL MAPPING WITHOUTH DIRECT CORTICAL STIMULATION AND WITH LITTLE REQUIRED COMMUNICATION should be:

--SYSTEM AND METHOD FOR CORTICAL MAPPING WITHOUT DIRECT CORTICAL STIMULATION AND WITH LITTLE REQUIRED COMMUNICATION--

Signed and Sealed this  
Twenty-eighth Day of January, 2020

Andrei Iancu  
*Director of the United States Patent and Trademark Office*